United States Patent [19]

Bettinger et al.

[11] 4,278,548

[45] Jul. 14, 1981

[54] CONTROL OF BIOLOGICAL GROWTH IN REVERSE OSMOSIS PERMEATORS

[75] Inventors: George E. Bettinger; Hermann W. Pohland; Lynn E. Applegate, all of Wilmington, Del.

[73] Assignee: E. I. Du Pont de Nemours and Company, Wilmington, Del.

[21] Appl. No.: 68,079

[22] Filed: Aug. 20, 1979

[51] Int. Cl.³ .............................................. B01D 13/00
[52] U.S. Cl. .................................... 210/636; 210/639; 210/654; 422/28; 422/37
[58] Field of Search ................ 210/22 R, 22 A, 22 C, 210/22 D, 23 R, 23 H, 23 F, 59, 257.2, 62, 63 R, 433 M, 64, 152, 195.2, 25, 96 M, 636, 639, 654; 422/28, 37, 48; 55/16, 158; 252/106

[56] References Cited

U.S. PATENT DOCUMENTS

| | | | |
|---|---|---|---|
| 2,443,429 | 6/1948 | Marks et al. | 210/11 |
| 3,215,627 | 11/1965 | Tools | 210/64 |
| 3,567,632 | 3/1971 | Richter et al. | 210/500 M |
| 3,589,998 | 6/1971 | Rice et al. | 210/23 H |
| 3,690,860 | 9/1972 | Salutsky | 210/64 |
| 3,992,301 | 11/1976 | Shippey et al. | 210/23 H |
| 4,148,606 | 4/1979 | Morita et al. | 422/21 |

FOREIGN PATENT DOCUMENTS

| | | | |
|---|---|---|---|
| 50-37268 | 7/1975 | Japan | 210/23 H |
| 51-13391 | 2/1976 | Japan | 210/23 H |

OTHER PUBLICATIONS

Hackh's Chem. Dictionary, 4th Ed., 1974, p. 620, J. Grant, McGraw-Hill Book Co.

Use's and Applications of Chemicals and Related Materials, T. Gregory, Reinhold Pub. Co., 1939, p. 550.

The Condensed Chem. Dictionary, G. Hawley, 9th Ed., Van Nostrand Reinhold Co., 1977, pp. 52, 452, 469, 797, 798.

Morris, William, The American Heritage Dictionary, Houghton Mifflin Co., Boston, 1975, pp. 288 and 1046.

*Primary Examiner*—Charles N. Hart
*Assistant Examiner*—David R. Sadowski

[57] ABSTRACT

Process for the control of bacterial growth in polyamide reverse osmosis membranes by treatment with iodide, hydrogen peroxide, or hydrogen peroxide derivatives.

6 Claims, No Drawings

CONTROL OF BIOLOGICAL GROWTH IN REVERSE OSMOSIS PERMEATORS

BACKGROUND OF THE INVENTION

Polyamide membranes and hollow fibers are used in a wide variety of reverse osmosis applications. The permselective properties of these membranes permit the purification of liquid streams to eliminate undesirable dissolved components. One important application is the purification of water used for industrial processes where dissolved components would contaminate process equipment or the product being prepared.

While currently available reverse osmosis units based on polyamide membranes are highly effective in their intended applications, the treatment of surface water such as that obtained from rivers and lakes has limited the useful life of such devices. The microorganisms found in such surface water tend to become imbedded and multiply in the polyamide membranes, causing clogging and fouling of the reverse osmosis unit. While a variety of disinfectants has been used to remove such microorganisms and inhibit their growth in other reverse osmosis membranes, most such disinfectants either rapidly degrade polyamide membranes or require an interruption of the operation of the reverse osmosis device. Accordingly, a need exists for the biological purification of reverse osmosis membranes based on an amide linkage during operation of the devices.

SUMMARY OF THE INVENTION

The instant invention provides an improved process for the continuous operation of reverse osmosis devices based on polyamide membranes which successfully inhibits the growth of microorganisms while not seriously damaging the polymeric structure of the membrane.

Specifically, the present invention provides an improvement in the process for continuously purifying a liquid process stream by passing it through at least one reverse osmosis module comprising a core member having a semipermeable polyamide membrane positioned in a manner whereby the liquid can permeate through the membrane producing flows of permeate and concentrate, which improvement comprises introducing into the process stream prior to its entering the reverse osmosis module about from 5 to 25 parts per million, based on the total volume of the process stream, of an additive selected from the group consisting of iodine, hydrogen peroxide, sodium persulfate, ammonium persulfate and sodium perborate, for a period of about from 30 minutes to 3 hours per 72 hours of operation.

DETAILED DESCRIPTION OF THE INVENTION

The present invention is applicable to the operation of reverse osmosis units based on polyamide membranes. Such membranes can be in the form of flat films or hollow fibers, and can be prepared from a wide variety of linear and aromatic polyamides. Representative films and reverse osmosis devices prepared from such films are described in detail in Richter & Hoehn, U.S. Pat. No. 3,567,632, hereby incorporated by reference.

The present invention is based on the discovery that the addition of iodine or hydrogen peroxide to the process stream before it enters the reverse osmosis device, for limited portions of the operating cycle, satisfactorily inhibits the growth of microorganisms while not degrading the structural integrity of the membrane polymer at an undesirable rate. In addition, hydrogen peroxide derivatives can also be used, including sodium persulfate, ammonium persulfate and sodium perborate. Other hydrogen peroxide derivatives can also be used within the scope of the present invention.

The iodine, hydrogen peroxide or hydrogen peroxide derivatives can be added to the process stream in a variety of convenient forms. The iodine can be added as elemental iodine. More preferably, when chlorine is present in the process stream, the iodine can be generated from an iodine salt such as potassium iodide or sodium iodide. The potassium iodide reacts with the chlorine generally used to reduce the microorganism count in the feed water before the process stream reaches the permeator. The potassium iodide reacts with the chlorine to form potassium chloride plus iodine. Alternatively, the iodine can be added directly in solution with an alcohol, for example, those having from one to four carbon atoms. Sodium persulfate is readily available in powder form, and can be added as an aqueous solution.

The iodine, hydrogen peroxide or hydrogen peroxide derivative is added in quantities to provide about from 1 to 25 parts per million in the process stream entering the permeator. The quantity of additive introduced will necessarily be adjusted depending on the quantity of chlorine still present in the process stream at the point of introduction. Because of the severe degradation of the polymer caused by chlorine, it is typically removed prior to entering the permeator. This is most frequently accomplished by adding sodium meta-bisulfite to the process stream to react with the residual chlorine and convert it to chloride ions that do not attack the membrane polymer. In the event that an excess of sodium meta-bisulfite is present, a portion of the iodine added to the process stream will react with the sodium meta-bisulfite and not be available for microorganism control. Accordingly, the indicated quantities of additive required for the instant process represent the amount introduced into the process stream in excess of that required to react with sodium meta-bisulfite ions still present in the process stream.

It has been found that less than 5 parts per million of additive have an undesirably low beneficial effect in microorganism control in the instant process, while quantities of the additive in excess of 25 parts per million provide little incremental benefit in microorganism control while adversely affecting polymer life. With the use of iodine as the additive, a concentration of about from 5 to 15 parts per million is preferred, while hydrogen peroxide and hydrogen peroxide derivative concentrations of 10 to 20 parts per million are preferred.

The additive is introduced into the continuous process stream for an average of about from 30 minutes to 3 hours per 72 hours of operation. However, for uniformity of the microorganism control, it is preferred that a single addition period be scheduled for each 24 to 72 hours of operation. With a single addition each 24 hours, a treatment time of about from 30 minutes to one hour is preferred. Longer addition periods are generally used when the addition is made once each 48 or 72 hours of operation.

The additive is introduced into the process stream before it enters the permselective device. Typically, a high-pressure pump is present in the system just prior to the permeator, and the present additives are conveniently introduced just before the high-pressure pump.

For convenience and economy of operation, the addition of potassium iodide can be used to replace all or part of the sodium meta-bisulfite normally used for chlorine control. Thus, sodium bisulfite can be diverted from its normal point of introduction to a point downstream from the permselective device for final treatment of product water before discharge or use of the water.

The instant invention results in the control of microorganism growth within polyamide permeators. While such permeators often exhibit markedly degraded performance within 4 weeks of operation when polluted surface water is desalinated, the use of the instant process typically permits continuous operation for periods of several months or longer. At the same time, the intermittent addition of iodine, sodium persulfate or hydrogen peroxide in accordance with the instant invention does not result in the polymer degradation characteristic of either chlorine disinfectants or the continuous use of other disinfectants. In addition, this procedure permits the inhibition of microorganism growth without the inconvenience of removing the permeator from its normal operation.

The present invention is further illustrated by the following specific examples, in which parts and percentages are by weight unless otherwise indicated.

EXAMPLE 1

Brackish water from a dammed estuary was purified using a 10 cm diameter permeator containing hollow polyamide filaments.

The brackish water was first pretreated by adding sodium hypochlorite to provide 5 parts per million of free chlorine at the end of the pretreatment. Colloidal solids in the water were coagulated by the addition of aluminum sulfate (alum). Solids were settled by passage through an upward flow, sludge blanket clarifier. The water was next passed through a sand-anthracite dual media filter, AG sand filter and finally a 10 micron particle size cartridge filter. The feed water was then dechlorinated by the addition of sodium metabisulfite in an amount equal to 15 parts per million.

An aqueous solution of potassium iodide was injected concomitantly with the sodium metabisulfite in an amount sufficient to generate 15 parts per million of iodine. After a 10 minute period, the sodium metabisulfite addition was stopped and dechlorination of the feed water effected by the potassium iodide alone.

The resulting pretreated water was passed through the permeator, which operated for a period of thirty days during which the potassium iodide was added for two hours per day; thirty days in which the potassium iodide was added for one hour per day; sixty days during which the potassium iodide was added for thirty minutes per day; and twenty days in which the potassium iodide was added for thirty minutes every other day. During this entire period of operation, no undesirable biological fouling was observed.

EXAMPLE 2

The general procedure of Example 1 is repeated, except that hydrogen peroxide is used in amounts sufficient to provide 15 parts per million of hydrogen peroxide instead of the 5 parts per million of potassium iodide, and the addition continued daily for two hours per day. A similar long term absence of biological fouling is observed.

COMPARATIVE EXAMPLE A

The general procedure of Example 1 is repeated, except that the addition of sodium metabisulfite is continued and potassium iodide is not added to the feed stream. Within four weeks the level of biological fouling reaches a level that requires a shut down and cleaning of the permeator.

We claim:

1. In the process for continuously purifying a liquid process stream by passing it through at least one reverse osmosis module comprising a core member having a semipermeable polyamide membrane positioned in a manner whereby the liquid permeates through the membrane producing flows of permeate and concentrate, the improvement which comprises inhibiting the growth of microorganisms in said liquid process stream and on the membrane by repeatedly introducing into the process stream prior to its entering the reverse osmosis module about from 5 to 25 parts per million, based on the total volume of the process stream, of an uncombined additive selected from the group consisting of iodine, hydrogen peroxide, sodium persulfate, ammonium persulfate and sodium perborate for a period of about from 30 minutes to 3 hours per 72 hours of operation, without interruption of the process stream.

2. A process of claim 1 wherein the additive consists essentially of iodine.

3. A process of claim 2 wherein the iodine is present in quantities of about from 5 to 15 parts per million.

4. A process of claim 1 wherein the additive consists essentially of hydrogen peroxide.

5. A process of claim 4 wherein the hydrogen peroxide is present in quantities of about from 10 to 20 parts per million.

6. A proces of claim 2 wherein the additive is introduced once every 24-hour period for about from 30 minutes to one hour.

* * * * *